United States Patent [19]

Todd

[11] Patent Number: 5,556,386
[45] Date of Patent: Sep. 17, 1996

[54] MEDICAL PRESSURE RELIEF VALVE

[75] Inventor: Robert J. Todd, Salt Lake City, Utah

[73] Assignee: Research Medical, Inc., Salt Lake City, Utah

[21] Appl. No.: 415,360

[22] Filed: Apr. 3, 1995

[51] Int. Cl.$^6$ .................................................. A61M 5/00
[52] U.S. Cl. .............................................. 604/247; 137/510
[58] Field of Search ..................................... 604/247, 249, 604/9, 30, 33, 34, 323, 335; 137/852, 853, 510

[56] References Cited

U.S. PATENT DOCUMENTS

| Re. 34,243 | 5/1993 | Gerber | 604/247 |
|---|---|---|---|
| 4,795,437 | 3/1989 | Schulte et al. | 604/247 |
| 5,052,900 | 10/1991 | Austin . | |
| 5,186,431 | 2/1993 | Tamari . | |

OTHER PUBLICATIONS

Circulatory Technology Inc. Product Brochure, 1995.
Sorin Biomedical Product Brochure, 1994.

*Primary Examiner*—Corrine M. McDermott
*Assistant Examiner*—N. Kent Gring
*Attorney, Agent, or Firm*—Workman Nydegger Seeley

[57] ABSTRACT

Pressure relief valve apparatus is disclosed for shunting fluids under conditions of overpressure, thereby preventing further increases in the pressure within a fluid delivery system. A presently preferred embodiment of the apparatus of the invention is formed of two components, a valve body member and a valve tube member. The valve body member is provided with first and second connector elements for use in connecting the pressure relief valve into a medical fluid delivery circuit. It is also provided with first and second bores passing through the first and second connector elements, respectively, and exiting at respective first and second exit ports on the side of the valve body member. A valve seat comprising a raised annular ridge around the circumference of the valve body member separates the first and second exit ports. The valve tube member is formed from an elastic material, preferably silicone tubing, and is placed in elastic tension over the valve body member so as to cover both exit ports and the valve seat. Under conditions of rest and low pressures, the valve tube member prevents fluid from passing between the two exit ports, but under conditions of overpressure, the valve tube member will stretch away from the valve seat, forming a gap therebetween through which fluid will flow.

14 Claims, 4 Drawing Sheets

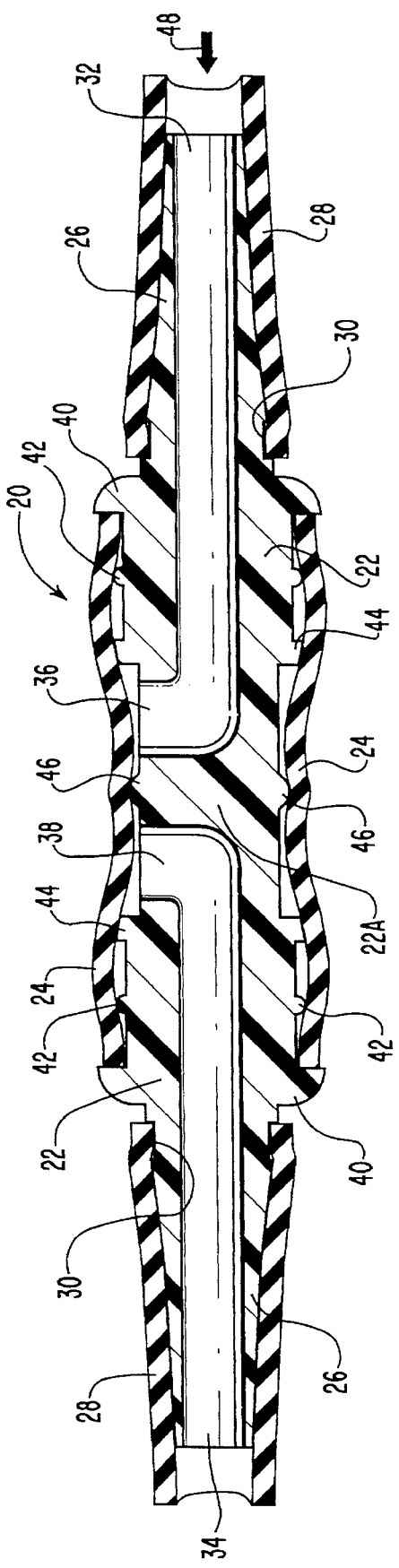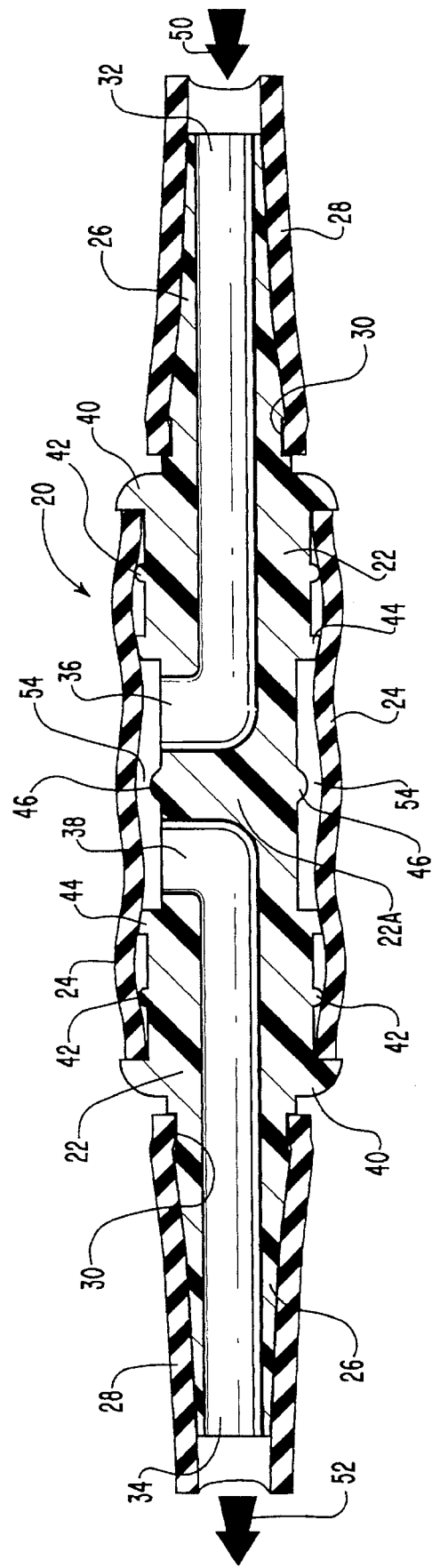

MEDICAL PRESSURE RELIEF VALVE

BACKGROUND OF THE INVENTION

1. Technical Field

The present invention is directed to pressure relief valves, and more particularly to pressure relief valves for medical applications using positive pressure pumps such as roller pumps.

2. Background Information

Many medical procedures utilize positive pressure pumps to move fluids to and from a patient. For example, cardiopulmonary bypass procedures require blood be moved from a patient to and through an external extracorporeal oxygenation circuit. During open heart surgery, it is necessary to deliver cardioplegia solution in order to maintain a patient's heart in a state of diastolic arrest. Kidney patients requiring dialysis treatments transfer blood through a dialysis machine for removal of toxins.

It has been a longstanding practice to utilize a roller pump to move fluids in medical applications. A roller pump uses a peristaltic action to advance fluids by moving a rotor in a rolling motion across the surface of tubing. The rolling motion of the rotor compresses the tubing against a support member, thereby pushing fluid ahead of the rotor. One advantage of a roller pump is the gentleness with which it pumps fluid through a length of tubing; this is particularly important when pumping fluids containing blood since less gentle treatment can result in lysis of the blood cells. Another advantage of roller pumps is that the fluid never touches the pump, permitting the pump to be reused by simply replacing the tubing for each new medical procedure.

Roller pumps are not without disadvantages. One problem arises from the ability of the roller pump to generate substantial pumping pressure. On occasion, a circuit through which fluid is desired to be pumped may become clogged, or more commonly it is simply closed off during setup and inadvertently left closed off when pumping is commenced. Typically, for example, a fluid circuit is primed with fluid so as to remove all air bubbles, and then closed off until it is time to pump the fluid. It occasionally happens that a medical team employing a roller pump will forget to open the appropriate valves before commencing operation of the roller pump. The high pressure generated by a roller pump can result in damage to system components. It can even result in an explosive separation of tubing from one or more components, resulting in an uncontrolled spraying of fluid contained in the tubing around the surgical area. If the closed valve is opened while excessive pressure exists, a high pressure flow can be delivered into the patient, potentially causing serious injury. If the tubing contains an obstruction, that obstruction may give way under increased pressure, and may be introduced into the patient, also potentially causing serious injury.

Because of these disadvantages of roller pumps, some medical practitioners have given up the significant advantages of roller pumps for other types of pumps that generate lower pressures. For example, centrifugal pumps are currently in wide use for the same uses as roller pumps because the pressures they will generate if blocked become self-limiting at pressures significantly less than those generated by roller pumps. Centrifugal pumps are subject to some of the same problems as roller pumps, however, such as generating higher than normal pressures when a blockage occurs, even though they are less likely than roller pumps to result in injury and are unlikely to cause explosive failure of the system components. Centrifugal pumps suffer from the significant disadvantage that they are more expensive to use than roller pumps. Since they operate by moving fluid directly through the pump, they must be replaced after a single use. By way of contrast, a roller pump may be reused indefinitely; only the associated tubing requires replacement after each procedure.

Various solutions have been sought to solve disadvantages such as those mentioned above. U.S. Pat. No. 5,052,900 (hereinafter sometimes referred to as the '900 patent), the disclosure of which is incorporated herein by reference, describes the introduction of a pressure relief valve at a location between the outlet and inlet ports to a positive pressure pump. This valve is shown as being formed of a length of tubing which is closed off by a pair of tubular members biased toward one another by elastic bands with sufficient force to seal the tube. Application of sufficient pressure will overcome the bias of the elastic bands, permitting fluid from the outlet port of the pump to recirculate through the pump, thereby stopping any further pressure increase within the system. Use of this type of valve is beneficial in concept because it is inexpensive to make, allowing its disposal after each use without adding unreasonable cost to the medical procedure.

It has been discovered that this approach is not fully functional in practice. For example, it has been found difficult to construct a valve according to the teachings of the '900 patent that has a strong enough elastic bias member to close the valve tubing, yet will allow that same tubing to open up before substantial pressures build up. Thus, it only partially solves the problem of a pressure increase within the system. This problem appears to be severely exacerbated when the valve has been stored for some period of time, since the tubing tends to adapt to its compressed condition, requiring even greater pressure before it will open. Hence, this type of valve has been a disappointment to many medical practitioners.

SUMMARY OF THE INVENTION

It is a primary object of the present invention to provide improved pressure relief valves suitable for use in medical applications.

It is a further object of the present invention to provide pressure relief valves that will operate reliably even after long periods of storage.

Yet another object of the present invention is to provide pressure relief valves capable of being constructed so as to operate at a particular pressure selected from a wide range of possible pressures.

Yet a further object of the present invention is to provide pressure relief valves that may be made economically enough to be disposed of after a single use.

Additional objects and advantages of the invention are set forth hereinbelow in the detailed description, or will be appreciated by the practice of the invention.

To achieve the foregoing objects, and in accordance with the invention as embodied and broadly described herein, the present invention provides a pressure relief valve for shunting fluids under conditions of overpressure, thereby preventing further increases in the pressure within a fluid delivery system.

A presently preferred embodiment of the apparatus of the invention is formed of two components, a valve body member and a valve tube member. The valve body member is provided with first and second connector elements for use in connecting the pressure relief valve into a medical fluid delivery or circulation system. It is also provided with first and second bores passing through the first and second connector elements, respectively, and exiting at respective first and second exit ports on the side of the valve body member. A valve seat comprising a raised annular ridge around the circumference of the valve body member separates the first and second exit ports.

The valve tube member of the present invention is formed from an elastic material, preferably silicone tubing, which is placed in elastic tension over the valve body member so as to cover both exit ports and the valve seat. Under low pressure conditions, the valve tube member prevents fluid from passing between the two exit ports, but under overpressure conditions the valve tube member will stretch away from the valve seat, forming a gap therebetween through which fluid will flow.

BRIEF DESCRIPTION OF THE DRAWINGS

In the accompanying drawings, which represent the best mode presently contemplated for carrying out the present invention:

FIG. 3 is a longitudinal cross-sectional view taken along the line 3—3 of FIG. 1 of the pressure relief valve, shown as it the valve would appear when under a pressure lower than the threshold at which the valve will be forced open.

FIG. 4 is a longitudinal cross-sectional view similar to that of FIG. 3, but showing the valve as it would appear when under a pressure greater than the threshold pressure required to cause the valve to operate.

DETAILED DESCRIPTION OF THE PREFERRED EMBODIMENT

The present invention provides improved pressure relief valves which are particularly useful as a protection against overpressure situations in connection with the use of positive pressure pumps, such as roller pumps, in medical applications.

A presently preferred embodiment of a pressure relief valve in accordance with the present invention is illustrated in FIGS. 1–4. In hindsight, pressure relief valve 20 is surprisingly simple, being formed of only two parts, a valve body member 22 and a valve tube member 24.

Figure 1:
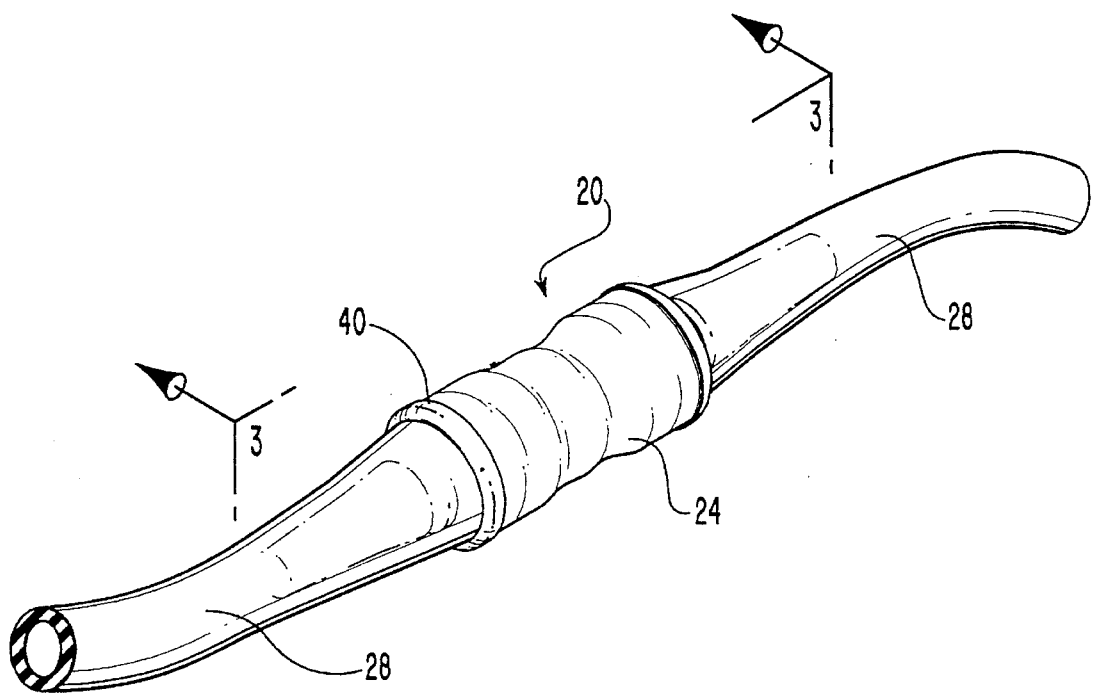
FIG. 1 is a perspective view of a presently preferred embodiment of a pressure relief valve in accordance with the present invention, shown attached to two pieces of tubing.
Figure 2:
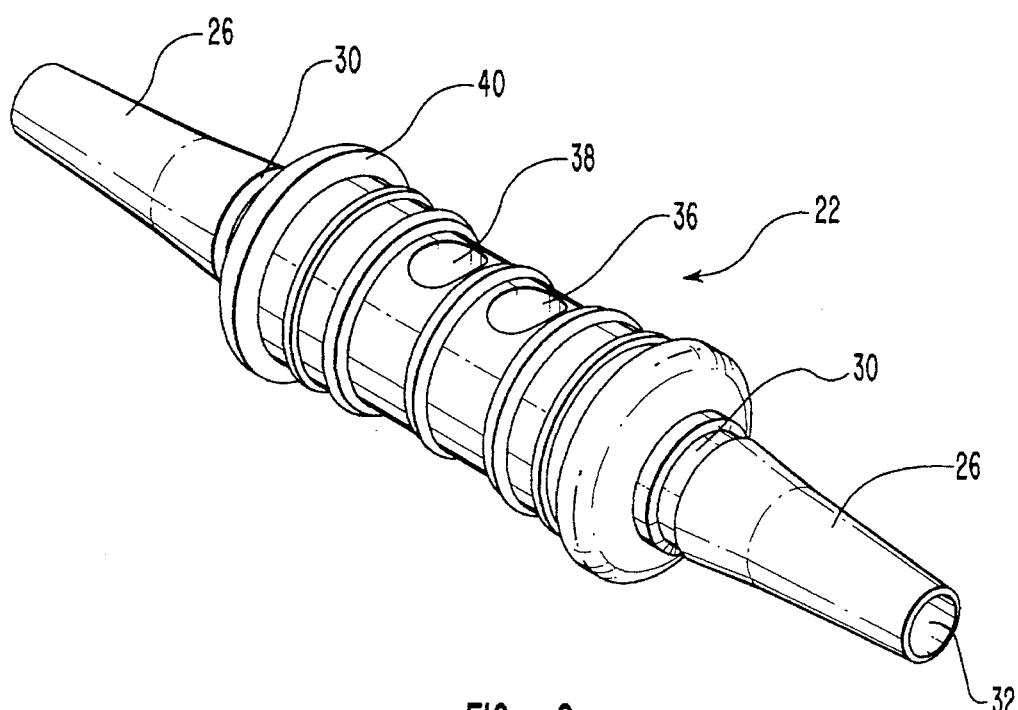
FIG. 2 is a perspective view of the valve body member of the pressure relief valve illustrated in FIG. 1.

The valve body member is illustrated in perspective view in FIG. 2. It may be observed in FIG. 2 that valve body member 22 is provided with a connector element 26 at each end which is suitable for attachment to a length of tubing 28 (See FIG. 1). It is preferred that connector element 26 be tapered from a diameter approximately the same as the inner diameter of tubing 28 to a larger diameter which places tubing placed thereover under tension. As illustrated, connector element 26 of the preferred embodiment has the basic appearance and construction of a standard luer-type connection. It may also be desirable to provide the surface of connector element 26 with one or more ridge elements 30 in order to further assist in maintaining tubing 28 securely in place under the particular pressure conditions under which pressure relief valve 10 will be used. In the form illustrated, it would be anticipated that tubing 28 would also be bonded to connector elements 26 in conventional fashion. Alternatively, connector elements 26 and tubing 28 would be provided with conventional luer lock fittings (not shown), permitting easy attachment and removal of the tubing. Both of these attachment methods are well known.

Valve body member 22 is also provided with a pair of axial bores 32 and 34 (see FIG. 3) which pass from the ends of the respective connector elements 26 to a location short of the middle of the valve body member, and then turn outward so they exit valve body member as exit ports 36 and 38, respectively. A barrier of solid material 22A (See FIG. 3) lies between bores 32 and 34 so that they do not communicate with each other. It will be appreciated that although the illustrated structure is presently preferred, alternative configurations can perform the same function, and hence would be equivalent to the configuration illustrated in the presently preferred embodiment. For example, the bores might follow a different shaped path than illustrated, more than one exit port might communicate with the axial portion of the bore around the circumference of the valve body member, or the bores and exit ports might assume different shapes than shown.

As noted above, the second component of pressure relief valve 20 is valve tube member 24. Valve tube member 24 should have an inner diameter smaller than the smallest outside diameter of valve body member 22. It is placed over valve body member 22 so as to cover both exit ports 36 and 38 under elastic tension. Valve tube member 24 is preferably formed from a length of silicone tubing, which material is preferred because it is readily available in various diameters and thicknesses, is inexpensive, can be stored for long periods with degradation, and has relatively consistent properties of elasticity. Other elastic tubing could be used, although it may not have all the advantages of silicone tubing. For example, standard surgical tubing is typically formed from latex, and suffers from a relatively short shelf life. Accordingly, latex tubing is not preferred, though it may be used if long shelf life is not important.

The preferred embodiment of pressure relief valve 10 is provided with a pair of opposing collars 40 against which the respective ends of valve tube member 24 abut. Collars 40 serve the functions of preventing valve tube member 24 from slipping off valve body member 22; provide a smooth surface which is less likely to catch on objects with which pressure relieve valve 20 may come in contact; and present an attractive appearance.

In order to insure pressure relieve valve 20 will not leak during use, the diameter of valve body member 22 in the region near each end of valve tube member 24 needs to be large enough to place the valve tube member under enough elastic tension to prevent leakage. It may also be desirable to provide one or more annular ribs 42 or 44 to further assist in sealing and securing the ends of valve tube member 24.

A valve seat 46 is located between exit ports 36 and 38, and presents a barrier to passage of fluid between the two exit ports. In the preferred embodiment, valve seat 46 is an annular ring. Of course, it will be readily appreciated in light of the teachings contained herein that many alternative constructions might be used without departing from the present invention. For example, the valve body member need not be cylindrical, nor does the valve seat need to pass around the entirety of the valve body member. All that is required is that the flow between the two exit ports be blocked by the valve seat and the valve tube member during low pressure conditions.

The diameter of valve seat 46 would typically be smaller than the diameter of the valve body member in the region near collars 40 and ribs 42 and 44 so that the valve tube member is pressed less tightly against the valve seat than at its ends. In addition, it is useful for the diameter of valve body member 22 in the region between ribs 42 and 44 and valve seat 46 to be smaller than other portions of the valve body member so as to form a open cavity between the exit ports and the surrounding valve tube member, thereby facilitating rapid transfer of fluid when the pressure relief valve is subjected to overpressure conditions.

Under conditions of rest, such as when no positive pressure or when a low positive pressure is introduced into one end of pressure relief valve 20, illustrated schematically in FIG. 3 by use of a small arrow 48 pointing toward bore 32, valve tube member 24 will rest against valve seat 46 under elastic tension, preventing any communication between exit ports 36 and 38. If for any reason the pressure increases above the particular threshold pressure for a particular pressure relief valve 20, as illustrated schematically in FIG. 4 through use of a large arrow 50 pointing toward bore 32, valve tube member 24 will bulge outwardly due to the increased pressure. This will open a gap 54 between valve tube member 24 and valve seat 46 through which fluid will flow from exit port 36 and into exit port 38. Fluid will then leave the pressure relief valve through bore 34, as indicated by arrow 52. At pressures close to that of the threshold pressure, the valve will only open slightly, resulting in only a small stream of fluid being pumped through the pressure relief valve. This is a useful feature in instances where there is a partial blockage because delivery of pumped fluid will not be totally prevented, but buildup of dangerous pressures will be avoided. In situations where the pressure continues to increase, gap 54 will continue to widen until it is finally large enough to accommodate a full flow of fluid from the associated pump, assuming that the pressure relief valve is large enough. This points out the need to obtain a pressure relief valve having characteristics, including maximum throughput, and a suitable threshold release pressure, which match a positive pressure pumping system with which the pressure relief valve is to be used.

The particular threshold pressure at which a pressure relief valve in accordance with the present invention will operate will depend upon a number of factors, such as the diameter of the valve tube member in comparison to the diameter of the valve body member; the wall thickness of the valve tube member; and the diameter of bore 32 and exit port 36. For cardiopulmonary bypass circuits, it will typically be desirable to commence opening the valve at about 500 millimeters of mercury pressure, and attain full pressure relief throughput (i.e., all fluid pumped by the cardiopulmonary bypass pump will circulate through the pressure relief valve) by the time the pressure increases to about 800 millimeters of mercury pressure. For cardioplegia delivery circuits, it is presently preferred that the valve commence operation at about 300 millimeters of mercury pressure. Control of factors such as those discussed above will permit a pressure relieve valve in accordance with the present invention to be formed that has virtually any threshold relief pressure desired. It will also be appreciated that a pressure relief valve constructed in accordance with the teachings of the present invention will maintain that threshold relief pressure even after substantial periods of storage.

Figure 5:
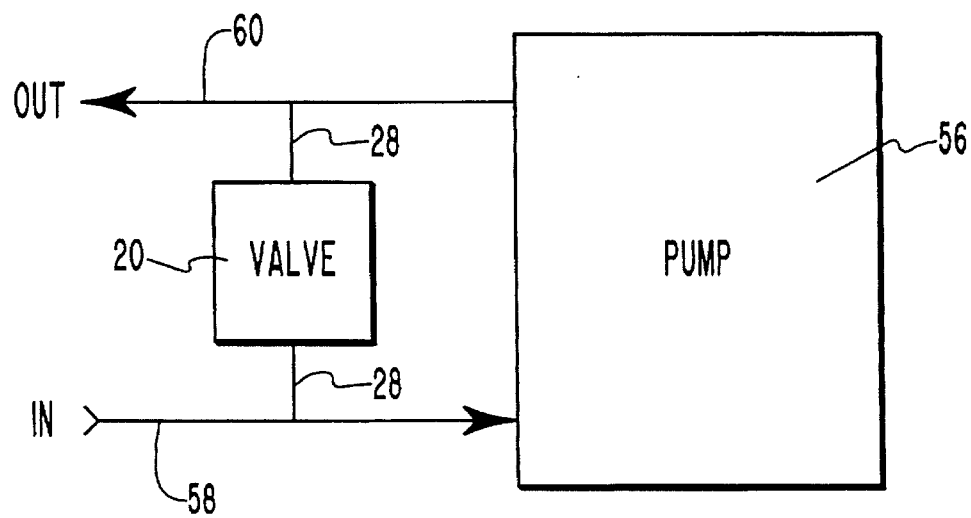
FIG. 5 is a schematic diagram showing one typical placement of the pressure relief valve of the present invention in relationship to a positive pressure pump in a cardiopulmonary bypass circuit.

FIG. 5 is a schematic diagram illustrating the preferred placement of the pressure relief valve of the present invention with respect to a positive pressure pump. FIG. 5 depicts a positive pressure pump 56, such as a roller pump or a centrifugal pump, having an input line 58 and an output line 60 which is intended to carry a fluid. FIG. 5 illustrates one typical configuration useful in cardiopulmonary bypass circuits. Pressure relief valve 20 and associated tubing 28 is connected to input line 58 and output line 60. Under typical operating conditions, pressure relief valve 20 will remain closed so that fluid will be pumped from input line 58, through pump 56, and out of output line 60. In the event of a blockage of output line 60, the pressure in output line 60 will increase. If that pressure increases to the threshold relief pressure of pressure relief valve 20, the valve will commence to operate in the manner discussed above, and will thereby permit fluid being pumped into output line 60 to shunt back into the input line 58. As the pressure continues to increase, the gap 54 between the valve seat and the valve tube element will become larger so as to accommodate an increased flow of fluid. Eventually, continued operation of pump 56 will cause pressure relief valve 20 to operate in a fully opened position, resulting in recirculation of all fluid pumped in the circuit without any further increase in pressure.

In setting up a system like that depicted in FIG. 5 it is important for most medical procedures that all tubing be primed with fluid so no air remains in the system. It has been discovered that a pressure relief valve in accordance with the present invention may be primed easily so as to remove all air bubbles. This is most easily accomplished by pinching valve tube member 24 in the vicinity of valve seat 46 in order to break the seal around the valve seat. Fluid may then easily pass through the valve, displacing any air found therein.

It has been discovered that the pressure relief valve of the present invention tends to exhibit a chattering or vibratory action and associated sound when operating under slight overpressure conditions. This provides an audio alarm at the time that an overpressure condition begins to occur.

Figure 6:
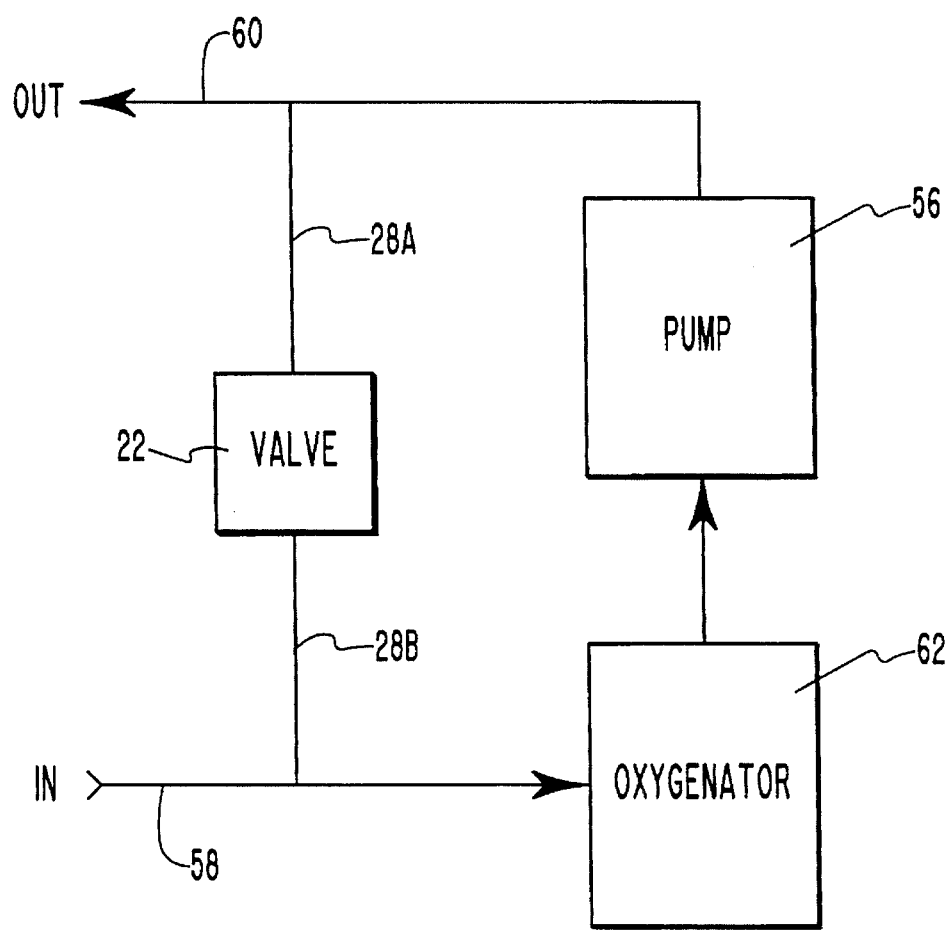
FIG. 6 is a schematic diagram showing an alternative typical placement of the pressure relief valve of the present invention in a cardiopulmonary bypass circuit.

FIG. 6 illustrates in schematic form another typical setup for cardiopulmonary bypass. FIG. 6 is identical to FIG. 5, except it shows that an oxygenator unit 62 may be located between tubing 28B leading out from pressure relief valve 20 and pump 56. Other setups will be apparent to those of ordinary skill in view of FIGS. 5 and 6.

Figure 7:
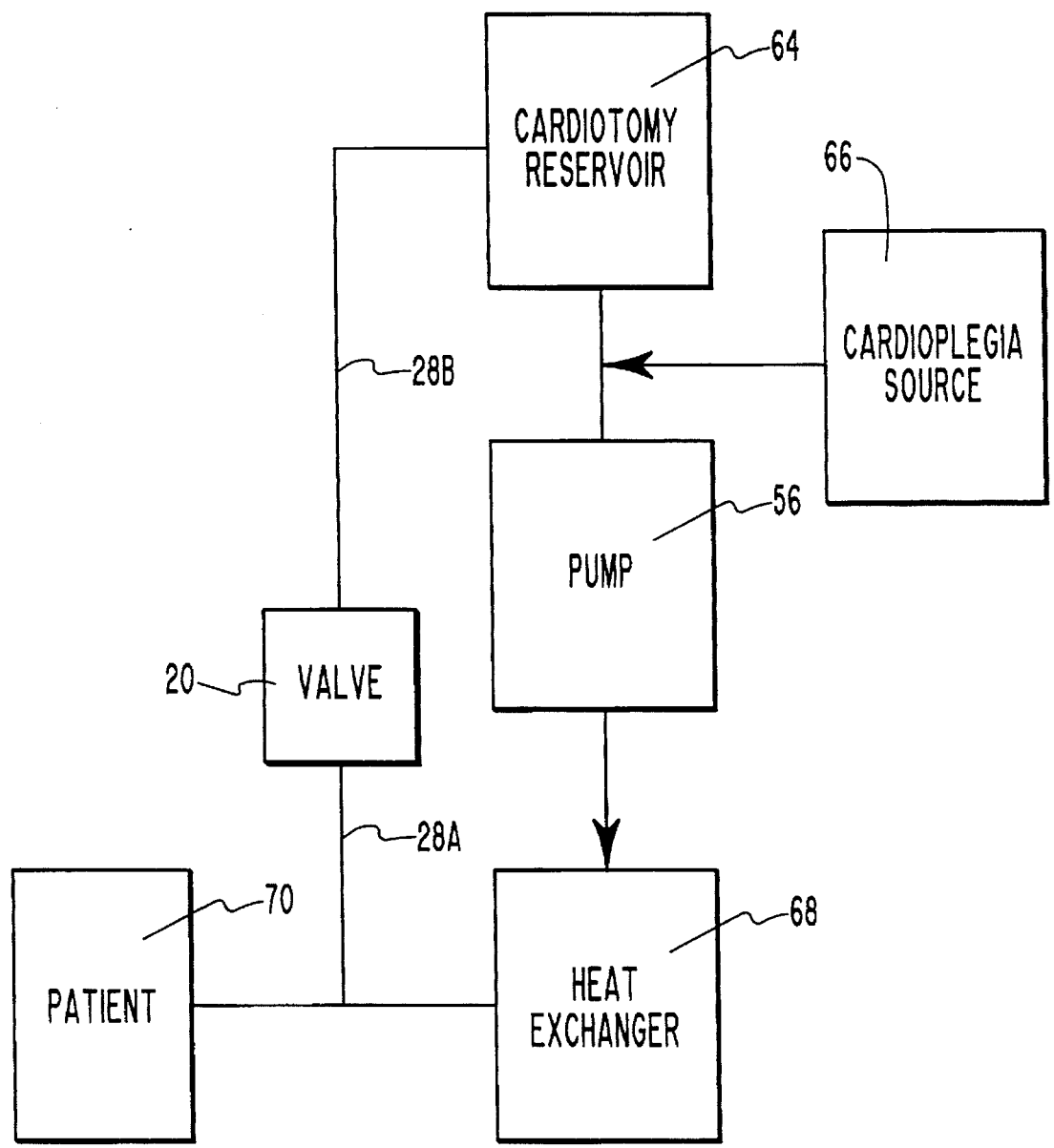
FIG. 7 is a schematic diagram showing a typical placement of the pressure relief valve of the present invention in a cardioplegia supply circuit.

A typical cardioplegia setup is illustrated in schematic form in FIG. 7. Blood from a cardiotomy reservoir 64 is pumped together with cardioplegia solution from a cardioplegia source 66, typically a bag of cardioplegia solution, through pump 56 and into a heat exchanger 68 where it is brought to a desired temperature for delivery to a patient 70. An overpressure condition will result in passage of the mixture of blood and cardioplegia solution through tubing 28A, pressure relief valve 20, tubing 28B, and back into the cardiotomy reservoir. Other setups, of course, could also be used.

The aforementioned advantages of the improved pressure relief valves of the present invention make them particularly suitable for use in medical applications. Even after substantial periods of storage they will function at the designed threshold relief pressure, and they can be designed to operate at most any desired threshold pressure. Despite these substantial advantages which make them more valuable than other solutions to the overpressure problem, they may be made economically enough to be disposed of after a single use. Although it is anticipated that the pressure relief valve of the present invention will most often be used with roller pumps, it will be appreciated that they will function in any positive pressure situation. Accordingly, they may be used with other positive pressure pumps, such as centrifugal pumps.

It will be appreciated that the present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by United States Patent is:

1. A pressure relief valve for preventing overpressure conditions in medical fluid delivery circuits utilizing positive pressure pumping, comprising;
    a valve body member, said valve body member including
        first and second connector elements for use in connecting the pressure relief valve into a medical fluid delivery circuit,
        first and second bores, said bores passing through the first and second connector elements, respectively, and exiting at respective first and second exit ports on the side of the valve body member, and
        a valve seat, said valve seat comprising a raised ridge element on the valve body member between said first and second exit ports; and
    a tubular valve member formed from an elastic material, said tubing valve member being placed in elastic tension in sealing engagement over the valve body member so as to cover the first and second exit ports and the valve seat.

2. A pressure relief valve as defined in claim 1, further comprising first and second portions around the valve body member near the ends of the tubular valve member having a greater diameter than at the location of the exit ports, thereby forming a cavity over the first and second exit ports.

3. A pressure relief valve as defined in claim 1, wherein the force of the elastic tension is such that the pressure relief valve will remain closed under pressures less than about 500 millimeters of mercury, but will commence to allow formation of a gap between the tubular valve member and the valve seat if the pressure increases above about 500 millimeters of mercury.

4. A pressure relief valve as defined in claim 1, wherein the force of the elastic tension is such that the pressure relief valve will remain closed under pressures less than about 300 millimeters of mercury, but will commence to allow formation of a gap between the tubular valve member and the valve seat if the pressure increases above about 300 millimeters of mercury.

5. A pressure relief valve as defined in claim 1, wherein the size of the first and second bores and the force of the elastic tension is such that the pressure relief valve is capable of shunting all of the fluid pumped in a medical delivery circuit at a pressure less than that at which damage to delivery circuit components will occur.

6. A pressure relief valve as defined in claim 1, wherein the valve body member is cylindrical and wherein the valve seat ridge element extends around the circumference of the cylindrical valve body member.

7. A medical fluid delivery circuits protected against harmful overpressure situations, comprising:
    a positive pressure pump; and
    a pressure relief valve, said pressure relief valve comprising:
        a valve body member, said valve body member including
            first and second connector elements for use in connecting the pressure relief valve into a medical fluid delivery circuit,
            first and second bores, said bores passing through the first and second connector elements, respectively, and exiting at respective first and second exit ports on the side of the valve body member, and
            a valve seat, said valve seat comprising a raised ridge element on the vane body member between said first and second exit ports; and
        a tubular valve member formed from an elastic material, said tubular valve member being placed in elastic tension in sealing engagement over the valve body member so as to cover the first and second exit ports and the valve seat.

8. A fluid delivery circuit as defined in claim 7, further comprising first and second portions around the valve body member near the ends of the tubular valve member having a greater diameter than at the location of the exit ports, thereby forming a cavity over the first and second exit ports.

9. A fluid delivery circuit as defined in claim 7, wherein the force of the elastic tension is such that the pressure relief valve will remain closed under pressures less than about 500 millimeters of mercury, but will commence to allow formation of a gap between the tubular valve member and the valve seat if the pressure increases above about 500 millimeters of mercury.

10. A fluid delivery circuit as defined in claim 7, wherein the force of the elastic tension is such that the pressure relief valve will remain closed under pressures less than about 300 millimeters of mercury, but will commence to allow formation of a gap between the tubular valve member and the valve seat if the pressure increases above about 300 millimeters of mercury.

11. A fluid delivery circuit as defined in claim 7, wherein the size of the first and second bores and the force of the elastic tension is such that the pressure relief valve is capable of shunting all of the fluid pumped in a medical delivery circuit at a pressure less than that at which damage to delivery circuit components will occur.

12. A fluid delivery circuit as defined in claim 7, wherein the pump is a roller pump.

13. A fluid delivery circuit as defined in claim 7, wherein the pump is a centrifugal pump.

14. A fluid delivery circuit as defined in claim 6, wherein the valve body member is cylindrical and wherein the valve seat ridge element extends around the circumference of the cylindrical valve body member.

* * * * *

UNITED STATES PATENT AND TRADEMARK OFFICE
CERTIFICATE OF CORRECTION

PATENT NO. : 5,556,386

DATED : September 17, 1996

INVENTOR(S) : ROBERT J. TODD

It is certified that error appears in the above-indentified patent and that said Letters Patent is hereby corrected as shown below:

Title page of patent, item [56], column 1, line 14 of references, "3/1989" should be --"1/1989"--

Col. 4, line 25, "altemative" should be --alternative--
Col. 4, line 43, "periods with degradation" should be --periods without degradation--
Col. 4, line 56, "relieve" should be --relief--
Col. 4, line 58, "relieve" should be --relief--
Col. 5, line 3, "altemative" should be --alternative--
Col. 6, line 1, "relieve" should be --relief--
Col. 7, line 39, "tubing" should be "tubular"
Col. 8, lines 4-7, claim number "6" should be claim number --13--
Col. 8, line 8, claim number "7" should be claim number --6--
Col. 8, line 23, "vane" should be --valve--
Col. 8, line 30, claim number "8" should be claim number --7--
Col. 8, line 30, "defined in claim 7" should be --defined in claim 6--
Col. 8, line 35, claim number "9" should be claim number --8--
Col. 8, line 35, "defined in claim 7" should be --defined in claim 6--
Col. 8, line 42, claim number "10" should be claim number --9--
Col. 8, line 42, "defined in claim 7" should be --defined in claim 6--
Col. 8, line 48, claim number "11" should be claim number --10--
Col. 8, line 48, "defined in claim 7" should be --defined in claim 6--

UNITED STATES PATENT AND TRADEMARK OFFICE
CERTIFICATE OF CORRECTION

PATENT NO.  : 5,556,386
DATED       : September 17, 1996
INVENTOR(S) : Robert J. Todd It is certified that error appears in the above-indentified patent and that said Letters Patent is hereby corrected as shown below:

Col. 8, line 54, claim number "12" should be claim number --11--
Col. 8, line 54, "defined in claim 7" should be --defined in claim 6--
Col. 8, line 56, claim number "13" should be claim number "12"
Col. 8, line 56, "defined in claim 7" should be --defined in claim 6--

Signed and Sealed this

Sixth Day of May, 1997

Attest:

Attesting Officer

BRUCE LEHMAN

Commissioner of Patents and Trademarks